United States Patent
Yang et al.

(10) Patent No.: US 10,231,661 B2
(45) Date of Patent: Mar. 19, 2019

(54) FOOD TASTE SIMULATION METHOD AND SYSTEM

(71) Applicant: BOE TECHNOLOGY GROUP CO., LTD., Beijing (CN)

(72) Inventors: Jiuxia Yang, Beijing (CN); Feng Bai, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 2 days.

(21) Appl. No.: 15/509,567

(22) PCT Filed: Aug. 16, 2016

(86) PCT No.: PCT/CN2016/095556
§ 371 (c)(1),
(2) Date: Mar. 8, 2017

(87) PCT Pub. No.: WO2017/076100
PCT Pub. Date: May 11, 2017

(65) Prior Publication Data
US 2017/0196495 A1 Jul. 13, 2017

(30) Foreign Application Priority Data
Nov. 4, 2015 (CN) .......................... 2015 1 0741805

(51) Int. Cl.
*A61B 5/00* (2006.01)
*A61N 1/00* (2006.01)
(Continued)

(52) U.S. Cl.
CPC .......... *A61B 5/4017* (2013.01); *A61B 5/0006* (2013.01); *A61B 5/04004* (2013.01);
(Continued)

(58) Field of Classification Search
CPC . A61B 5/4017; A61B 5/4277; A61B 5/04004; A61B 5/0006; G16H 10/60;
(Continued)

(56) References Cited

FOREIGN PATENT DOCUMENTS

| CN | 1913936 A | 2/2007 |
|---|---|---|
| CN | 103210411 A | 7/2013 |

(Continued)

OTHER PUBLICATIONS

Search Report and Written Opinion dated Nov. 28, 2016 from State Intellectual Property Office of the P.R. China.
(Continued)

*Primary Examiner* — Scott M. Getzow
(74) *Attorney, Agent, or Firm* — Dilworth & Barrese, LLP.; Michael J. Musella, Esq.

(57) ABSTRACT

A food taste simulation method, applied in a food taste simulation system, comprising: determining food information of target food according to a food simulation trigger signal when receiving the food simulation trigger signal; determining airflow for simulating the taste of the target food according to the food information; and releasing the airflow through an airflow chip disposed in the oral cavity according to the airflow. The safety of food simulation is improved and the effect of food simulation is enriched in this method. A food taste simulation system is also provided.

20 Claims, 6 Drawing Sheets

(51) Int. Cl.

| | | |
|---|---|---|
| *G16H 10/60* | (2018.01) | |
| *G16H 50/70* | (2018.01) | |
| *A61B 5/04* | (2006.01) | |
| *A61N 1/05* | (2006.01) | |
| *A61N 1/36* | (2006.01) | |
| *G06K 9/62* | (2006.01) | |
| *A61B 5/0484* | (2006.01) | |
| *G06F 19/00* | (2018.01) | |

(52) U.S. Cl.
CPC ........ *A61B 5/04847* (2013.01); *A61B 5/4277* (2013.01); *A61B 5/4836* (2013.01); *A61N 1/00* (2013.01); *A61N 1/0548* (2013.01); *A61N 1/36014* (2013.01); *G06F 19/00* (2013.01); *G06K 9/6201* (2013.01); *G16H 10/60* (2018.01); *G16H 50/70* (2018.01); *A61B 2503/12* (2013.01)

(58) Field of Classification Search
CPC ... G16H 50/70; G06F 19/3443; G06F 19/322; G06K 9/6201; A61N 1/0548; A61N 1/36014

See application file for complete search history.

(56) References Cited

FOREIGN PATENT DOCUMENTS

| CN | 103544346 A | 1/2014 |
|---|---|---|
| CN | 105396221 A | 3/2016 |

OTHER PUBLICATIONS

Hiroo Iwata, etc., Food simulator: a haptic interface for biting Virtual Reality; 2004, Proceedings, IEEE, Mar. 31, 2004 (Mar. 31, 2004) pp. 51-55.

Chen Dan, Tast simulator is successfully developed and manufactured in Japan, Science and Technology Daily Aug. 2, 2003 (Aug. 2, 2003) the whole text.

First Chinese Office Action dated Jun. 19, 2017

FOOD TASTE SIMULATION METHOD AND SYSTEM

TECHNICAL FIELD

Embodiments of the present disclosure relate to a food taste simulation method and a food taste simulation system.

BACKGROUND

The temptation of food is always difficult to resist, but uncontrolled diet will not only cause physical discomfort but also cause health problems such as overnutrition and over-standard body mass index (BMI).

In the relevant prior art, in order to avoid excessive intake of food while satisfying people's taste buds, the research personnel has developed a taste simulation device. The device can control current and temperature and transmit the current and the temperature to the tongue. The taste simulation device allows a user to feel sour, sweet, bitter, salty, or the like by stimulating the tongue of the user through current and temperature.

However, the taste simulation device in the relevant prior art needs to stimulate the tongue of the user through current and temperature, has potential safety hazards, and has single taste simulation effect.

SUMMARY

In order to solve the problems in the prior art, the present disclosure provides a food taste simulation method and system.

According to at least one embodiment of this disclosure, a food taste simulation method is provided, applied in a food taste simulation system, comprising: determining food information of target food according to a food simulation trigger signal when receiving the food simulation trigger signal; determining airflow for simulating the taste of the target food according to the food information; and releasing the airflow through an airflow chip disposed in the oral cavity according to the airflow.

For example, the velocity and the consumption of the airflow for simulating the taste of the target food are determined according to the food information; and the airflow is released by the airflow chip disposed in the oral cavity according to the velocity and the consumption of the airflow.

For example, the method further comprising: determining target odor molecules for simulating the odor of the target food according to the food information; and releasing the target odor molecules.

For example, the step of determining the food information of the target food according to the food simulation trigger signal when receiving the food simulation trigger signal includes: acquiring an electroencephalogram (EEG) signal of the human body; comparing the EEG signal with food signals prestored in a database; determining the EEG signal as the food simulation trigger signal when the EEG signal is the same with any food signal prestored in the database; and determining the food information of the target food corresponding to the food simulation trigger signal according to the preset corresponding relationship between the food signals and food information.

For example, the step of releasing the target odor molecules includes; releasing the target odor molecules through an odor releaser and/or an odor release chip disposed in the oral cavity.

For example, the food information includes identifications of ingredients; and the step of determining the airflow for simulating the taste of the target food according to the food information includes: calculating the number of the identifications of the ingredients in the food information of the target food; and determining the airflow for simulating the taste of the target food according to the identification of the ingredient, when the number of the identifications of the ingredients is equal to 1.

For example, the food information also includes a cooking method of food; and the step of determining the airflow for simulating the taste of the target food according to the food information includes: determining the airflow for simulating the taste of the target food by preset pattern recognition approach according to the identifications of the ingredients and the cooking method of the food, when the number of the identifications of the ingredients is greater than 1.

For example, the food information includes identifications of ingredients and identifications of tastes; and the step of determining the target odor molecules for simulating the odor of the target food according to the food information includes: calculating the number of the identifications of the ingredients in the food information of the target food; and determining the target odor molecules according to the identification of the taste when the number of the identifications of the ingredients is equal to 1.

For example, the food information also includes a cooking method of food; and the step of determining the target odor molecules for simulating the odor of the target food according to the food information includes: determining the target odor molecules by preset pattern recognition approach according to the identifications of the ingredients, the identifications of the tastes, and the cooking method of the food, when the number of the identifications of the ingredients is greater than 1.

For example, the food signals prestored in the database are electric signals; and the step of comparing the EEG signal with the food signals prestored in the database includes: comparing the waveform of the EEG signal with the waveforms of the electric signals of food prestored in the database.

For example, the food signals prestored in the database are logical signals; and the step of comparing the EEG signal with the food signals prestored in the database includes: converting the EEG signal into a logical signal; and comparing the converted logical signal with the logical signals of food prestored in the database.

According to at least one embodiment of this disclosure, a food taste simulation system, comprising: a signal processing device and an airflow chip disposed in the oral cavity, wherein the signal processing device is configured to determine food information of target food according to a food simulation trigger signal when receiving the food simulation trigger signal, determine airflow for simulating the taste of the target food according to the food information, and send signals for indicating the airflow to the airflow chip; and the airflow chip is configured to receive the signals for indicating the airflow, and release the airflow according to the signals of the airflow.

For example, the signal processing device is configured to determine the velocity and the consumption of the airflow for simulating the taste of the target food according to the food information, and send signals for indicating the velocity and the consumption of the airflow to the airflow chip; and the airflow chip is configured to receive the signals for indicating the velocity and the consumption of the airflow, and release the airflow according to the velocity and the consumption of the airflow.

For example, the system further comprising: an odor release device, wherein the signal processing device is also configured to determine target odor molecules for simulating the odor of the target food according to the food information, and send signals for indicating the target odor molecules to the airflow chip; and the odor release device is configured to receive the signals for indicating the target odor molecules, and release the target odor molecules.

For example, the system further comprising: an EEG acquisition device, wherein the EEG acquisition device is configured to acquire an EEG signal of the human body and send the EEG signal to the signal processing device; and the signal processing device is also configured to: compare the EEG signal with the food signals prestored in the database; determine the EEG signal as the food simulation trigger signal when the EEG signal is the same with any food signal prestored in the database; and determine the food information of the target food corresponding to the food simulation trigger signal according to the preset corresponding relationship between the food signals and food information.

For example, the odor release device includes: an odor releaser or an odor release chip disposed in the oral cavity; and the odor release device is also configured to: release the target odor molecules through the odor releaser and/or the odor release chip.

For example, the food information includes identifications of ingredients; and the signal processing device is also configured to: calculate the number of the identifications of the ingredients in the food information of the target food; and determine the airflow for simulating the taste of the target food according to the identification of the ingredient, when the number of the identifications of the ingredients is equal to 1.

For example, the food information also includes a cooking method of food; and the signal processing device is also configured to: determine the airflow for simulating the taste of the target food by preset pattern recognition approach according to the identifications of the ingredients and the cooking method of the food, when the number of the identifications of the ingredients is greater than 1.

For example, the food information includes identifications of ingredients and identifications of tastes; and the signal processing device is also configured to: calculate the number of the identifications of the ingredients in the food information of the target food; and determine the target odor molecules according to the identification of the taste when the number of the identifications of the ingredients is equal to 1.

For example, the food information also includes a cooking method of food; and the signal processing device is also configured to: determine the target odor molecules by preset pattern recognition according to the identifications of the ingredients, the identifications of the tastes and the cooking method of the food, when the number of the identifications of the ingredients is greater than 1.

For example, the food signals prestored in the database are electric signals; and the signal processing device is also configured to: compare the waveform of the EEG signal with the waveforms of the electric signals of food prestored in the database.

For example, the food signals prestored in the database are logical signals; and the signal processing device is also configured to: convert the EEG signal into a logical signal; and compare the converted logical signal with the logical signals of food prestored in the database.

For example, the airflow chip includes: a signal receiving layer, a gas generating layer and a gas release layer; the signal receiving layer is configured to receive the signals sent by the signal processing device; the gas generating layer is configured to be preset with basic elements for generating gas and/or a catalyst for accelerating gas generation; and the gas release layer is configured to release substances generated by the gas generating layer according to the instruction of the signals received by the signal receiving layer.

For example, the odor release device includes: containers for storing odor molecules; and the odor release device processes the target odor molecules stored in the containers after receiving the signals for indicating the target odor molecules sent by the signal processing device, so that the target odor molecules can be released into the air.

For example, the odor release device further includes: a fan configured to generate airflow when releasing the target odor molecules, so as to promote the release of the target odor molecules.

BRIEF DESCRIPTION OF THE DRAWINGS

In order to make the embodiments of the disclosure apparent, the drawings related to the embodiments of the disclosure will be described briefly. Apparently, the described embodiments are just a part of the embodiments of the disclosure. For those skilled in the art, he or she can obtain other figure(s) according to these figures, without any inventive work.

FIG. 1-2 is a flowchart of the food taste simulation method provided by the embodiment of the present disclosure;

FIG. 2-1 is a flowchart of another food taste simulation method provided by the embodiment of the present disclosure;

FIG. 2-2 is a flowchart of a method for determining food information of target food, provided by the embodiment of the present disclosure;

FIG. 2-3 is a flowchart of a preset pattern recognition approach provided by the embodiment of the present disclosure;

FIG. 3-1 is a schematic structural view of a food taste simulation system provided by the embodiment of the present disclosure;

FIG. 3-2 is a schematic structural view of an airflow chip in the embodiment of the present disclosure;

FIG. 3-3 is a schematic structural view of another food taste simulation system provided by the embodiment of the present disclosure; and FIG. 3-4 is a schematic diagram of an odor release device in the embodiment of the present disclosure.

DETAILED DESCRIPTION

For more clear understanding of the objectives, technical proposals and advantages of the present disclosure, further detailed description will be given below to the embodiments of the present disclosure with reference to the accompanying drawings.

Figure 1:
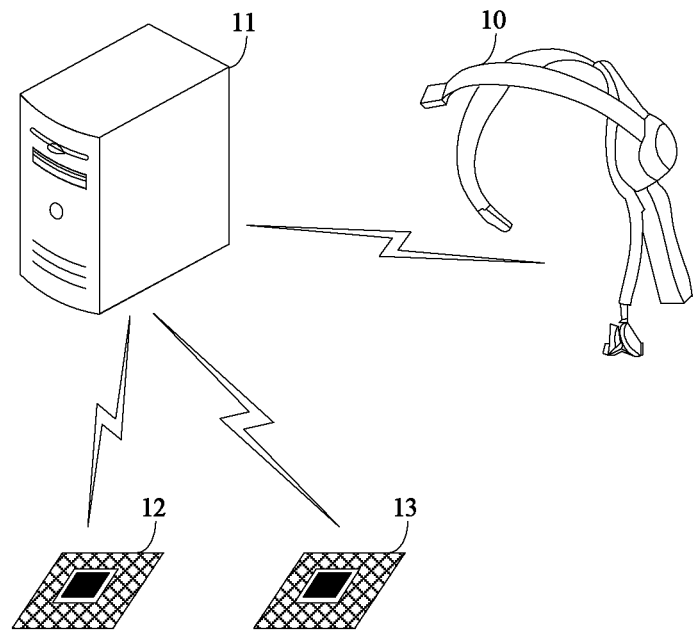
FIG. 1-1 is a schematic diagram of a food taste simulation system involved in a food taste simulation method provided by the embodiment of the present disclosure.

FIG. 1-1 is a schematic diagram of a food taste simulation system involved in a food taste simulation method provided by the embodiment of the present disclosure. As illustrated in FIG. 1-1, the system may comprise: an EEG (electroencephalogram) acquisition device 10, a signal processing device 11, an airflow chip 12 and an odor release device 13. The signal processing device 11 is respectively connected with the EEG acquisition device 10, the airflow chip 12 and the odor release device 13 via wired or wireless network. Wherein, the EEG acquisition device 10 may be a cap structure, e.g., a helmet, and may also be a headset structure or electronic skin attached to the brain of the human body.

EEG is current generated on the outside of cells of the cerebral cortex by potential difference formed between cell populations of the cerebral cortex in the activity of the brain. The EEG records changes of electric waves in the activity of the brain. Thus, when a user wants to eat something, an EEG signal of the user will also change correspondingly. In the system as shown in FIG. 1-1, the EEG acquisition device 10 may acquire an EEG signal of the human body in real time and send the EEG signal to the signal processing device 11. The signal processing device 11 is configured to compare the EEG signal with food signals stored in a database, determine target food corresponding to the EEG signal, and hence determine the velocity and the consumption of airflow for simulating the taste of the target food, and target odor molecules for simulating the odor of the target food. The signal processing device 11, for instance, may be implemented by software, hardware or firmware, for instance, may be achieved by a general processor chip (e.g., a central processing unit (CPU)), and may also be achieved by a special processor chip such as a programmable logic device (PLD) and a field-programmable gate array (FPGA). The signal processing device 11 sends the signal to the airflow chip, and finally the airflow chip 12 releases the airflow according to the instruction of the signal. The odor release device 13 is configured to release the target odor molecules, so as to achieve the effect of simulating the taste and the odor of food thought of by the user. The airflow chip 12, for instance, may be a microprocessor chip or chip set. The odor release device 13, for instance, may include containers for storing odor molecules, processes the target odor molecules stored in the containers after receiving signals for indicating the target odor molecules sent by the signal processing device, so that the target odor molecules can be released into the air. Moreover, for instance, the odor release device may also include a fan which is configured to generate airflow when releasing the target odor molecules, so as to promote the release of the target odor molecules.

Figures 1, 2:
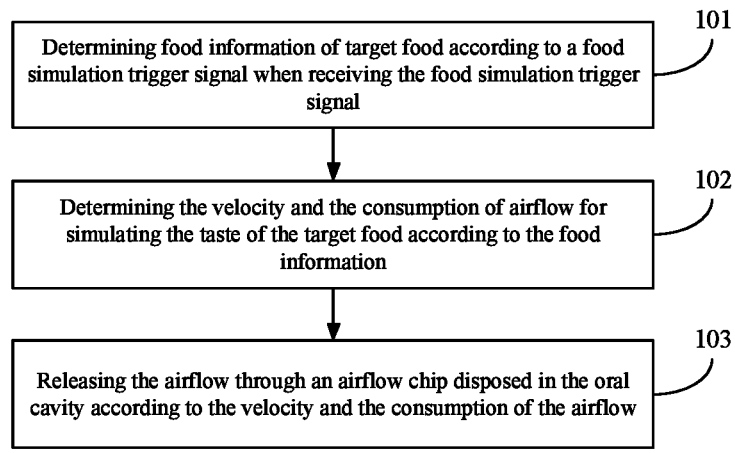

FIG. 1-2 is a flowchart of a food taste simulation method provided by the embodiment of the present disclosure. The method may be applied in the system as shown in FIG. 1-1. As illustrated in FIG. 1-2, the method comprises:

S101: determining food information of target food according to a food simulation trigger signal when receiving the food simulation trigger signal;

S102: determining the velocity and the consumption of airflow for simulating the taste of the target food according to the food information; and S103: releasing the airflow through an airflow chip disposed in the oral cavity according to the velocity and the consumption of the airflow.

In summary, the embodiment of the present disclosure provides the food taste simulation method. The food taste simulation system may determine the food information of the target food according to the food simulation trigger signal when receiving the food simulation trigger signal, and further determine the airflow for simulating the taste of the target food according to the food information, for instance, determining the velocity and the consumption of the airflow, and finally may release the airflow through the airflow chip disposed in the oral cavity according to the velocity and the consumption of the airflow. The food taste simulation method provided by the embodiment of the present disclosure adopts gas to simulate the taste of various foods, does not require current and temperature stimulation, improves the safety of food simulation, and enriches the effect of food simulation. Of course, it should be understood by those skilled in the art that in order to simulate the taste of the target food, the determination of the velocity or the consumption of the airflow is only an example, and other properties of the airflow, e.g., the flow direction, the coverage in the oral cavity, and the vortex mode, may also be determined, so that the taste of the food can be more realistically simulated.

For instance, the method further comprises:

determining target odor molecules for simulating the odor of the target food according to the food information, and releasing the target odor molecules.

For instance, the step of determining the food information of the target food according to the food simulation trigger signal when receiving the food simulation trigger signal includes: acquiring an EEG signal of the human body, comparing the EEG signal with food signals prestored in a database, determining the EEG signal as the food simulation trigger signal when the EEG signal is the same with any food signal prestored in the database, and determining the food information of the target food corresponding to the food simulation trigger signal according to the corresponding relationship between the preset food signals and food information.

For instance, the step of releasing the target odor molecules includes: releasing the target odor molecules through an odor releaser or an odor release chip disposed in the oral cavity.

For instance, the food information includes identifications of ingredients and a cooking method of food; and the step of determining the velocity and the consumption of the airflow for simulating the taste of the target food according to the food information includes:

calculating the number of the identifications of the ingredients in the food information of the target food; and determining the velocity and the consumption of the airflow for simulating the taste of the target food according to the identification of the ingredient, when the number of the identifications of the ingredients is equal to 1.

For instance, when the number of the identifications of the ingredients is greater than 1, the velocity and the consumption of the airflow for simulating the taste of the target food are determined by preset pattern recognition approach according to the identifications of the ingredients and the cooking method of the food.

For instance, the food information includes identifications of ingredients, identifications of tastes, and a cooking method of food; and the step of determining the target odor molecules for simulating the odor of the target food according to the food information includes: calculating the number of the identifications of the ingredients in the food information of the target food, determining the target odor molecules according to the identification of the taste when the number of the identifications of the ingredients is equal to 1, and determining the target odor molecules by preset pattern recognition approach according to the identifications of the ingredients, the identifications of the tastes, and the cooking method of the food when the number of the identifications of the ingredients is greater than 1.

For instance, the food signals prestored in the database are electric signals; and the step of comparing the EEG signal with the food signals prestored in the database includes: comparing the waveform of the EEG signal with the waveforms of the electric signals of food prestored in the database.

For instance, the food signals prestored in the database are logical signals; and the step of comparing the EEG signal with the food signals prestored in the database includes: converting the EEG signal into a logical signal, and comparing the logical signal with the logical signals of food prestored in the database.

In summary, the embodiment of the present disclosure provides the food taste simulation method. The food taste simulation system may determine the food information of the target food according to the food simulation trigger signal when receiving the food simulation trigger signal, and further determine the velocity and the consumption of the airflow for simulating the taste of the target food according to the food information, and finally may release the airflow through the airflow chip disposed in the oral cavity according to the velocity and the consumption of the airflow. As the airflow is generated by gas harmless to the human body, the food taste simulation method and system provided by the embodiment of the present disclosure have higher safety, can also simulate the odor of the food through the odor release device, and hence enrich the effect of food simulation.

FIG. 2-1 is a flowchart of another food taste simulation method provided by the embodiment of the present disclosure. The method may be applied in the system as shown in FIG. 1-1. As illustrated in FIG. 2-1, the method comprises:

S201: allowing a signal processing device to determine food information of target food according to a food simulation trigger signal when receiving the food simulation trigger signal.

In the embodiment, the signal processing device may store the corresponding relationship between food simulation signals and food information. The food information may include identifications of ingredients, identifications of tastes, a cooking method of food, etc. When receiving the food simulation trigger signal, the signal processing device may determine the food information of the target food corresponding to the food simulation trigger signal according to the stored corresponding relationship. Wherein, the food simulation trigger signal may be an EEG signal and may also be a data signal sent to the signal processing device when a user directly inputs the name of the target food into a terminal and the terminal processes the information inputted by the user.

FIG. 2-2 is a flowchart of a method for determining food information of target food, provided by the embodiment of the present disclosure. As illustrated in FIG. 2-2, when the food simulation trigger signal is an EEG signal, the step of determining the food information of the target food may include:

S2011: allowing an EEG acquisition device to acquire the EEG signal of the human body.

In the embodiment of the present disclosure, the food taste simulation system may acquire the EEG signal of the human body in real time through the EEG acquisition device 10 as shown in FIG. 1-1. The EEG acquisition device may include a plurality of sensors for detecting and acquiring EEG The plurality of sensors may be wet electrodes and may also be dry electrodes. No limitation will be given here in the embodiment of the present disclosure. Wherein, the specific process of acquiring the EEG signal of the human body through the EEG acquisition device may refer to relevant prior art, and no further description will be given here in the embodiment of the present disclosure.

S2012: allowing the EEG acquisition device to send the EEG signal to a signal processing device.

As the EEG signal is generally weak, after acquiring the EEG signal, the EEG acquisition device may perform filtering and differential amplification on the EEG signal at first, and then send the processed EEG signal to the signal processing device by wired connection or wireless connection such as Bluetooth and Wireless Fidelity (WI-FI).

S2013: allowing the signal processing device to compare the EEG signal with food signals prestored in a database.

In the embodiment of the present disclosure, the database of the signal processing device may store a plurality of preset food signals. The food signals may be electric signals and may also be logical signals. When the food signals prestored in the database are electric signals, the signal processing device may directly compare the waveform of the received EEG signal with the waveforms of the electric signals of food prestored in the database. When the food signals prestored in the database are logical signals, the signal processing device may perform analog-to-digital conversion on the received EEG signal at first, convert the EEG signal into a logical signal, and then compare the converted logical signal with the logical signals of food prestored in the database.

Illustratively, supposing that the food signals prestored in the database of the signal processing device are logical signals, when the obtained logical signal corresponding to the EEG signal is 00110100 after the signal processing device performs analog-to-digital conversion on the received EEG signal, the signal processing device may compare the logical signal 00110100 with the logical signals of all the foods stored in the database one by one.

S2014: determining the EEG signal as the food simulation trigger signal when the EEG signal is the same with any food signal prestored in the database.

When the EEG signal is the same with any food signal stored in the database, the signal processing device may determine the EEG signal as the food simulation trigger signal, namely the EEG signal is a signal relevant to food. Illustratively, if the logical signal 00110100 of food is stored in the database of the signal processing device, the signal processing device may determine the EEG signal as the food simulation trigger signal.

S2015: determining the food information of the target food corresponding to the food simulation trigger signal according to the preset corresponding relationship between the signals and food information.

In the embodiment of the present disclosure, the corresponding relationship between the signals and the food information may also be stored in the database of the signal processing device. As the ingredients of different foods are different, some foods consist of a single ingredient, for example, apple and lemon, but some foods are formed by a plurality of ingredients via specified cooking method, for example, Tomato Omelette (Tomato Fried with Eggs), in which the taste and the odor of the single ingredient may be directly determined, but the taste and the odor of the food including the plurality of ingredients must comprehensively consider the factors such as the amount of each ingredient and a cooking method. Therefore, the food information stored in the database may include identifications of ingredients, identifications of tastes, and a cooking method of food, in which the cooking method of the food may include stir-frying, pan-frying, steaming, boiling, roasting, etc. When determining the received EEG signal as the food simulation trigger signal, the signal processing device may further determine the food information of the target food corresponding to the food simulation trigger signal according to the corresponding relationship between the signals and the food information. Illustratively, the corresponding relationship between the signals and the food information stored in the database may be as shown by the Table 1, wherein food corresponding to a logical signal 00110100 is apple, and corresponding food information includes an identification of an ingredient: 01, and an identification of a taste: 011; and food corresponding to a logical signal 00110110 is Tomato Omelette, and corresponding food information includes identifications of ingredients: 03 and 04, identifications of tastes: 031 and 041, and a cooking method of food: stir-frying, in which 03 and 031 may respectively represent the identification of the ingredient and the identification of the taste corresponding to tomato, and 04 and 041 may respectively represent the identification of the ingredient and the identification of the taste corresponding to egg.

TABLE 1

| | | Food Information | | |
|---|---|---|---|---|
| Signal | Food | Identifications of Ingredients | Identifications of Tastes | Cooking Method of Food |
| 00110100 | Apple | 01 | 011 | / |
| 00110101 | Lemon | 02 | 021 | / |
| 00110110 | Tomato Omelette | 03, 04 | 031, 041 | Stir-frying |

S202: allowing the signal processing device to determine the velocity and the consumption of airflow for simulating the taste of the target food according to the food information.

In the embodiment of the present disclosure, the signal processing device may store the corresponding relationship between the identifications of the ingredients and airflow information for simulating the taste of the ingredients, in which the airflow information includes the consumption and the velocity of airflow. Therefore, after determining the food information of the target food, the signal processing device may calculate the number of the identifications of the ingredients in the food information of the target food at first. When the number of the identifications of the ingredients is equal to 1, the signal processing device may determine the velocity and the consumption of the airflow for simulating the taste of the target food according to the identifications of the ingredients and the preset corresponding relationship between the identifications of the ingredients and the airflow information for simulating the taste of the ingredients.

Illustratively, supposing that the corresponding relationship between the identifications of the ingredients and the airflow information for simulating the taste of the ingredients prestored in the database is as shown by the Table 2, the velocity of airflow corresponding to the identification of the ingredient 01 (namely an identification of apple) is 10 ml per min, and the consumption is 10 ml; and the velocity of airflow corresponding to the identification of the ingredient 02 (namely an identification of lemon) is 7 ml per min, and the consumption is 10 ml . If the target food determined by the signal processing device is apple, the food information of the target food is: the identification of the ingredient: 01, and the identification of the taste: 011. As the number of the ingredient identifications is 1 in the food information, namely the target food is food consisting of a single ingredient, the signal processing device may directly determine the velocity of the airflow for simulating the taste of the target food: apple to be 10 ml per min and the consumption to be 10 ml according to the identification of the ingredient 01 in the food information and the corresponding relationship as shown by the Table 2.

TABLE 2

| Identifications | Airflow Information | |
|---|---|---|
| of Ingredients | Velocity | Consumption |
| 01 | 10 ml per min | 10 ml |
| 02 | 7 ml per min | 10 ml |
| 03 | 4 ml per min | 8 ml |
| 04 | 8 ml per min | 12 ml |

Figures 1, 2:
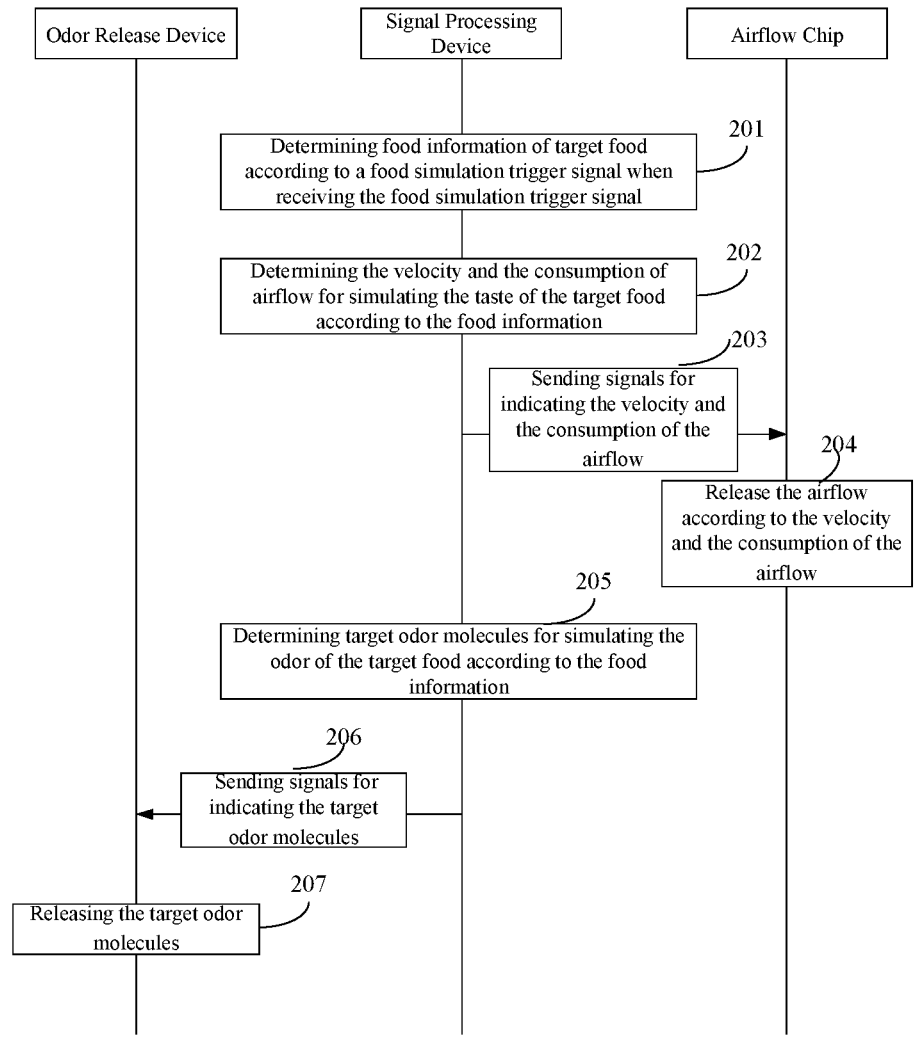
Figure 2:
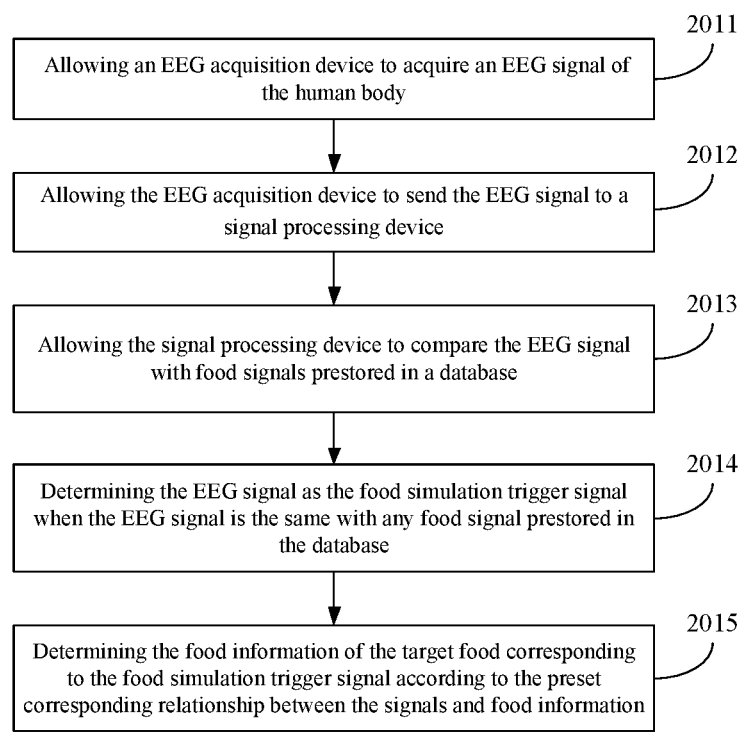
Figures 2, 3:
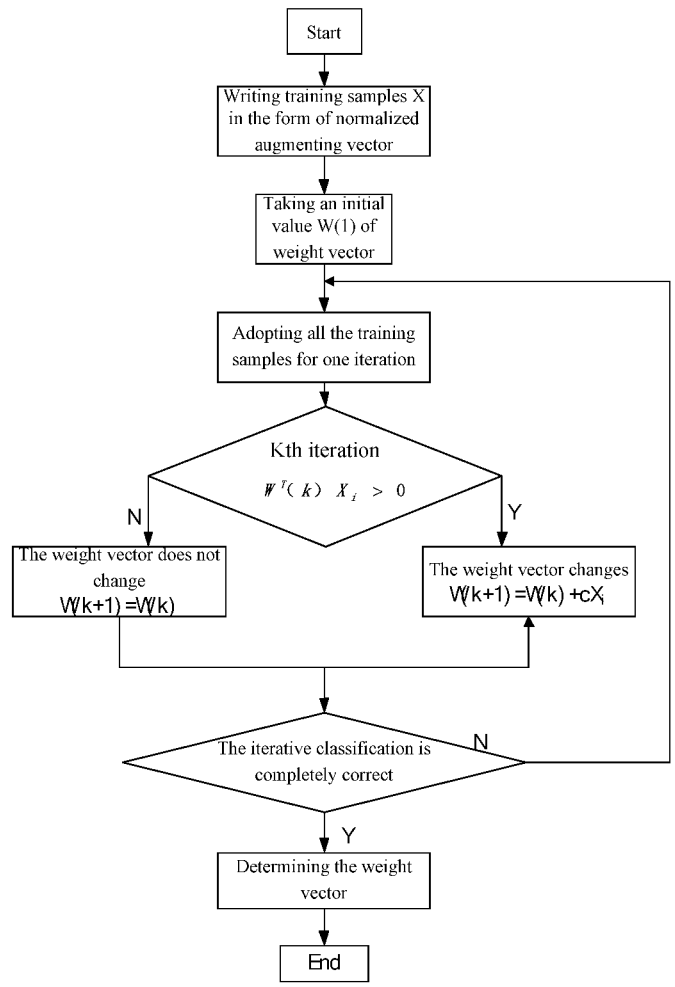

When the number of the identifications of the ingredients is greater than 1, the signal processing device may determine the velocity and the consumption of the airflow for simulating the taste of the target food by preset pattern recognition approach according to the identifications of the ingredients and the cooking method of the food in the food information of the target food. FIG. 2-3 is a flowchart of a preset pattern recognition approach provided by the embodiment of the present disclosure. The pattern recognition approach may be perceptron approach. The perceptron approach is created on the basis of the perceptron criterion function put forward by Rosenblatt. As illustrated in FIG. 2-3, in the approach, the signal processing device may take the identifications of the ingredients as training samples X, and the training sample $X=\{X_1, X_2, \ldots, X_i, \ldots, X_N\}$, in which N refers to the number of the identifications of the ingredients; the amount of each ingredient is taken as a weight vector W, and $W=\{W_1, W_2, \ldots, W_i, \ldots, W_N\}$; c refers to the preset correction coefficient in the approach; and the cooking method of the food such as stir-frying, pan-frying and cooking is taken as an environment variable of the approach for input, in which the environment variable may specifically include parameters such as the cooking temperature and the cooking duration corresponding to each cooking method. Subsequently, the signal processing device may continuously change the amount of each ingredient, namely continuously changing the weight vector of each sample in the training samples X, and then different weight vectors are adopted for multiple iterative computations. For instance, the weight vector of the $k^{th}$ iteration may be represented as W(k). When iterative classification is completely correct, the weight vector of this iteration is determined as the target amount of each ingredient. The iteration threshold L may also be preset in the signal processing device. When the training sample iterates for L times, the signal processing device may determine the weight vector W(L) after the $L^{th}$ iteration as the target amount of each ingredient. Wherein, the specific steps of determining the weight vector by the perceptron approach may refer to relevant prior art, and no further description will be given here in the embodiment of the present disclosure.

After determining the target amount of each ingredient, the signal processing device may calculate the proportion of the target amount of each ingredient in the total amount of all the ingredients, and determine the velocity and the consumption of the airflow by the following formula (1) according to the proportion of each ingredient:

wherein, $V_t$, $C_t$ respectively refer to the velocity and the consumption of the $$\begin{cases} v_t = \sum_{i=0}^{N} a_i v_i \\ c_t = \sum_{i=0}^{N} a_i c_i \end{cases} \quad (1)$$

airflow for simulating the taste of the target food; N refers to the number of the identifications of the ingredients, namely the number of the types of the ingredients; $a_i$ refers to the proportion of the target amount of the ith ingredient in the total amount of all the ingredients; and $V_i$ and $C_i$ respectively refer to the velocity and the consumption of gas corresponding to the ith ingredient stored in the signal processing device.

Illustratively, supposing that the food information of the target food determined by the signal processing device is: the identifications of the ingredients: 03 and 04; the identifications of the tastes: 031 and 041; the cooking method of the food: stir-frying, as the number of the identifications of the ingredients is 2, greater than 1, in the food information of the target food: Tomato Omelette, namely the target food is not food consisting of a single ingredient, the signal processing device may, in accordance with the pattern recognition approach as shown in FIG. 2-3, take the identifications of the ingredients: 03 and 04 as the training samples X, and take the cooking method of the food: stir-frying as a known condition for input. Supposing that the judgment after two iterations is correct, and at this point, the target amount of each ingredient is that: the target amount of the identification of the ingredient 03 is 75 (the unit is gram), and the target amount of the identification of the ingredient 04 is 25, the signal processing device may calculate the proportion of the target amount of each ingredient in the total amount of all the ingredients: the proportion of the identification of the ingredient 03 is 0.75, and the proportion of the identification of the ingredient 04 is 0.25. Subsequently, the signal processing device may determine the velocity and the consumption of airflow for simulating the taste of the target food: Tomato Omelette by the formula (1) according to the corresponding relationship between the identifications of the ingredients and the airflow information as shown by the Table 2:

namely the velocity of the airflow for simulating the taste of the target $$\begin{cases} v_t = \sum_{i=0}^{N} a_i v_i = 0.75 \times 4 + 0.25 \times 8 = 5 \\ c_t = \sum_{i=0}^{N} a_i c_i = 0.75 \times 8 + 0.25 \times 12 = 9 \end{cases}$$

food: Tomato Omelette, determined by the signal processing device according to the preset pattern recognition approach, is 5 ml per min, and the consumption of the airflow is 9 ml.

In actual application, the signal processing device may also generate alternative velocity and consumption according to the results obtained after each iteration in the pattern recognition approach, and release airflow generated according to the alternative velocity and consumption into the oral cavity of the user, so that the user can evaluate the alternative velocity and consumption. When the signal processing device receives determination information triggered by the user according to preset operation, the weight vector determined in the iteration may be taken as the target amount of each ingredient. Moreover, the target amount is stored in the database, so that the signal processing device can directly determine the velocity and the consumption for simulating the taste of the target food according to the target amount of each ingredient, when receiving the food information of same target food again. Wherein, the preset operation may be voice operation and may also be key operation, EEG or other means. No limitation will be given here in the embodiment of the present disclosure.

It should be noted that the approach about the velocity and the consumption of the airflow for simulating the taste of the target food may also be determined by specific ingredients and the cooking method of food. The embodiment of the present disclosure is only illustrative.

S203: allowing the signal processing device to send signals for indicating the velocity and the consumption of the airflow to an airflow chip.

In the embodiment of the present disclosure, the food taste simulation system may also include an airflow chip disposed in the oral cavity of the user. When determining the velocity and the consumption of the airflow for simulating the taste of the target food, the signal processing device may send the signals for indicating the velocity and the consumption of the airflow to the airflow chip. Illustratively, the signals sent to the airflow chip by the signal processing device may be: velocity: 10 ml per min, and consumption: 10 ml.

S204: allowing the airflow chip disposed in the oral cavity to release the airflow according to the velocity and the consumption of the airflow.

The airflow chip may generate and release preset gas according to the velocity and the consumption of the airflow. The preset gas may be gas harmless to the human body, e.g., oxygen, or a small amount of inert gas, e.g., carbon dioxide and helium gas.

Wherein, the airflow chip may include a plurality of functional layers, for instance, a signal receiving functional layer, a gas generating functional layer and a gas release functional layer. Each functional layer may correspondingly achieve different functions, wherein, the signal receiving functional layer is configured to receive signals sent by the signal processing device, and the gas generating functional layer is preset with a plurality of basic elements such as carbon, hydrogen, oxygen and helium for generating gas, and may also be provided with a catalyst for accelerating gas generation. When receiving the signals, the airflow chip may generate preset gas such as oxygen through the gas generating functional layer, and then may release the preset gas through the gas release functional layer according to the velocity and the consumption indicated by the signals. The gas flows in the oral cavity of the human body to form airflow, so that the human body can feel the food in the oral cavity, and hence the effect of simulating the taste of the food can be achieved. Illustratively, supposing that the velocity of the airflow indicated in the signal sent by the signal processing device is 10 ml per min and the consumption is 10 ml, the airflow chip disposed in the oral cavity may generate preset gas according to the signals and release the gas in the oral cavity at the speed of 10 ml per min, and the consumption of the released gas may be 10 ml, so that the user can feel the taste of chewing apple.

S205: allowing the signal processing device to determine target odor molecules for simulating the odor of the target food according to the food information.

The signal processing device may also store the corresponding relationship between the identifications of the tastes and odor molecules for simulating the odor of ingredients. As similar to the processing flow in the step S202, after determining the food information of the target food, the signal processing device may calculate the number of the identifications of the ingredients in the food information of the target food at first. When the number of the identifications of the ingredients is equal to 1, the signal processing device may determine target odor molecules for simulating the odor of the target food from the prestored corresponding relationship between the identifications of the tastes and the odor molecules for simulating the odor of the ingredients according to the identifications of the tastes in the food information.

Illustratively, the corresponding relationship between the identifications of the tastes and gas for simulating the odor of the ingredients stored in the database may be as shown by the Table 3, wherein odor molecules corresponding to the identification of the taste 011 (namely the identification of the taste corresponding to apple) include butyl butyrate, ethyl acetate and hexanol, and odor molecules corresponding to the identification of the taste 021 (namely the identification of the taste corresponding to lemon) include limonene and citral. When the target food is apple, the food information of the target food: apple, determined by the signal processing device is: the identification of the ingredient: 01, and the identification of the taste 011. As the number of the identifications of the ingredients in the food information is 1, namely the target food is food consisting of a single ingredient, the signal processing device may directly determine the target odor molecules for simulating the odor of the target food: apple to be butyl butyrate, ethyl acetate and hexanol according to the identification of the taste 011 in the food information and the corresponding relationship as shown by the Table 3.

TABLE 3

| Identification of Taste | Odor Molecules |
|---|---|
| 011 | Butyl Butyrate, Ethyl Acetate, Hexanol |
| 021 | Limonene, Citral |
| 031 | Lycopene |
| 041 | Ethyl Benzene, Butyl Benzene |

When the number of the identifications of the ingredients is greater than 1, the signal processing device may determine the target odor molecules for simulating the odor of the target food by the pattern recognition approach as shown in FIG. 2-3 according to the identifications of the ingredients and the cooking method of the food in the food information of the target food. In the approach, the signal processing device may take the identifications of the ingredients as the training samples X, take the amount of each ingredient as the weight vector W, and take the cooking method of the food as the environment variable of the approach for input, and subsequently, may continuously change the amount of each ingredient and adopt different weight vectors for multiple iterative computations of the training samples X, and determine the weight vector of the iteration as the target amount of each ingredient when the judgment is correct. Wherein, the specific process of determining the target amount of each ingredient by the signal processing device may refer to the step S202. No further description will be given here in the embodiment of the present disclosure. After determining the target amount of each ingredient in the target food, the signal processing device may calculate the proportion of the target amount of each ingredient in the total amount of all the ingredients, and determine the proportion of each odor molecule in the target odor molecules for simulating the odor of the target food according to the odor molecules corresponding to the taste identification of each ingredient and the proportion of each ingredient.

Illustratively, supposing that the food information of the target food determined by the signal processing device is: the identifications of the ingredients: 03 and 04, the identifications of the taste: 031 and 041, and the cooking method of the food: stir-frying, as the number of the identifications of the ingredients in the food information of the target food: Tomato Omelette, is 2, greater than 1, namely the target food is not food consisting of a single ingredient, the signal processing device may, in accordance with the pattern recognition approach as shown in FIG. 2-3, take the identifications of the ingredients 03 and 04 as the training samples X, and take the cooking method of the food: stir-frying as a known condition for input. Supposing that the judgment after two iterations is correct, and at this point, the target amount of each ingredient is that: the target amount of the identification of the ingredient 03 is 75 and the target amount of the identification of the ingredient 04 is 25, the calculated proportion of the identification of the ingredient 03 is 0.75, and the proportion of the identification of the ingredient 04 is 0.25. Therefore, the signal processing device may determine that the odor molecules for forming the target odor molecules include: lycopene, ethyl benzene and butyl benzene according to the corresponding relationship between the identifications of the tastes and the odor molecules as shown by the Table 3, wherein the proportion of lycopene in the target odor molecules is 0.75, and the proportion of ethyl benzene and butyl benzene in the target odor molecules is 0.25. That is to say, the target odor molecules for simulating the odor of the target food: Tomato Omelette, determined by the signal processing device according to the preset pattern recognition approach, is composed of 75% lycopene and 25% ethyl benzene and butyl benzene.

S206: allowing the signal processing device to send signals for indicating the target odor molecules to an odor release device.

After determining the target odor molecules, the signal processing device may send the signals for indicating the target odor molecules to the odor release device, so that the odor release device can release the target odor molecules. Illustratively, the signals sent by the signal processing device to the odor release device may be identifications corresponding to the target odor molecules: butyl butyrate, ethyl acetate and hexanol.

S207: allowing the odor release device to release the target odor molecules.

In the embodiment of the present disclosure, the odor release device may be an odor releaser or an odor release chip disposed in the oral cavity. A plurality of odor molecules for simulating different odors may be prestored in the odor release device. When receiving the signals for indicating the target odor molecules sent by the signal processing device, the odor release device may process the target odor molecules indicated in the signals by current stimulation, heating or other means, so that the target odor molecules can be released into the air, and hence the effect of simulating the odor of the target food can be achieved. Illustratively, supposing that the odor releaser is an odor release chip disposed in the oral cavity and the signal sent by the signal processing device and received by the odor release chip includes the identification corresponding to the target odor molecules: butyl butyrate, ethyl acetate and hexanol, the odor release chip may determine the target odor molecules to be butyl butyrate, ethyl acetate and hexanol according to the identification, and stimulate the three target odor molecules by the current generated in the chip, so that the three target odor molecules can be released into the oral cavity of the user, and hence the user can smell something like apple.

It should be noted that in actual application, the odor release chip and the airflow chip may be integrated into a same chip, and the target odor molecules released by the odor release chip may be more quickly released into the oral cavity of the human body when driven by the gas released by the airflow chip, so that the user can simultaneously feel the taste and the odor of the food, and hence the effect of food simulation can be enriched.

In summary, the embodiment of the present disclosure provides the food taste simulation method. The food taste simulation system may determine the food information of the target food according to the food simulation trigger signal when receiving the food simulation trigger signal, and further determine the velocity and the consumption of the airflow for simulating the taste of the target food according to the food information, and finally may release the airflow through the airflow chip disposed in the oral cavity according to the velocity and the consumption of the airflow. The food taste simulation method provided by the embodiment of the present disclosure adopts gas to simulate the taste of various foods, does not require current and temperature stimulation, improves the safety of food simulation, and enriches the effect of food simulation.

It should be noted that the sequence of the steps of the food taste simulation method provided by the embodiment of the present disclosure may be properly adjusted, and the steps may also be correspondingly added or reduced as required. Illustratively, the steps S205 to S207 are executed before the step S202. Any change that may be easily thought of by those skilled in the art within the technical scope disclosed in the present disclosure shall all fall within the scope of protection of the present disclosure. No further description will be given here.

FIG. 3-1 is a schematic structural view of a food taste simulation system provided by the embodiment of the present disclosure. As illustrated in FIG. 3-1, the system comprises: a signal processing device 301 and an airflow chip 302 disposed in the oral cavity.

Wherein, the signal processing device 301 may be a server or a terminal with signal processing capacity, for example, a mobile phone, a computer and a wearable device. The signal processing device 301 may also be a signal processing module integrated into the terminal. The airflow chip 302 may be disposed on the user's tooth by means of e-skin and may also be disposed on the user's gum or false tooth. As illustrated in FIG. 3-2, the airflow chip 302 may include a plurality of functional layers, for instance, a signal receiving functional layer 3021, a gas generating functional layer 3022 and an odor release functional layer 3023. Each functional layer may correspondingly achieve different functions, wherein the signal receiving functional layer 3021 is configured to receive signals sent by the signal processing device, and the odor generating functional layer 3022 is preset with a plurality of basic elements such as carbon, hydrogen, oxygen and helium for generating gas, and may also be provided with a catalyst for accelerating gas generation. When receiving the signals, the airflow chip may generate preset gas such as oxygen through the gas generating functional layer 3022, and then may release the preset gas according to the velocity and the consumption indicated by the signals through the gas release functional layer 3023.

The gas flows in the oral cavity of the human body to form airflow, so that the human body can feel the food in the oral cavity, and hence the effect of simulating the taste of the food can be achieved.

The signal processing device 301 is configured to determine food information of target food according to a food simulation trigger signal when receiving the food simulation trigger signal, determine airflow, e.g., velocity and consumption, for simulating the taste of the target food according to the food information, and send signals for indicating the velocity and the consumption of the airflow to the airflow chip. Of course, it should be understood by those skilled in the art that in order to simulate the taste of the target food, the determination of the velocity or the consumption of the airflow is only an example, and other properties of the airflow, e.g., the flow direction, the coverage in the oral cavity, and the vortex mode, may also be determined, so that the taste of the food can be more realistically simulated.

The airflow chip 302 is configured to receive the signals for indicating the velocity and the consumption of the airflow and release the airflow according to the velocity and the consumption of the airflow.

In summary, the food taste simulation system may determine the food information of the target food according to the food simulation trigger signal when receiving the food simulation trigger signal, and further determine the velocity and the consumption of the airflow for simulating the taste of the target food according to the food information, and finally may release the airflow through the airflow chip disposed in the oral cavity according to the velocity and the consumption of the airflow. The food taste simulation system provided by the embodiment of the present disclosure adopts gas to simulate the taste of various foods, does not require current and temperature stimulation, improves the safety of food simulation, and enriches the effect of food simulation.

FIG. 3-3 is a schematic structural view of another food taste simulation system provided by the embodiment of the present disclosure. As illustrated in FIG. 3-3, the system comprises: a signal processing device 301, an airflow chip 302 disposed in the oral cavity, an odor release device 303 and an EEG acquisition device 304.

The signal processing device 301 is configured to determine food information of target food according to a food simulation trigger signal when receiving the food simulation trigger signal, determine the velocity and consumption of airflow for simulating the taste of the target food according to the food information, and send signals for indicating the velocity and the consumption of the airflow to the airflow chip.

The airflow chip 302 is configured to receive the signals for indicating the velocity and the consumption of the airflow and release the airflow according to the velocity and the consumption of the airflow.

The signal processing device 301 is also configured to determine target odor molecules for simulating the odor of the target food according to the food information, and send signals for indicating the target odor molecules to the airflow chip.

The odor release device 303 is configured to receive the signals for indicating the target odor molecules and release the target odor molecules.

The EEG acquisition device 304 is configured to acquire an EEG signal of the human body and send the EEG signal to the signal processing device. The signal processing device 301 is also configured to:

compare the EEG signal with food signals prestored in a database;

determine the EEG signal as the food simulation trigger signal when the EEG signal is the same with any food signal prestored in the database; and determine the food information of the target food corresponding to the food simulation trigger signal according to the preset corresponding relationship between the signals and food information.

Figures 1, 3:
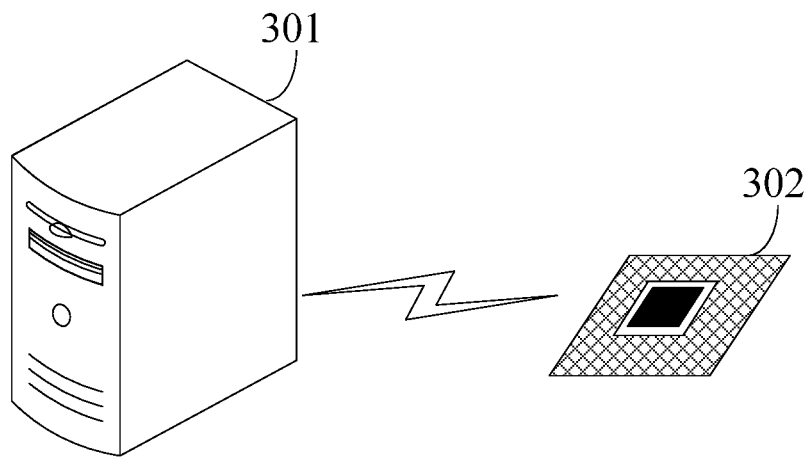
Figures 2, 3:
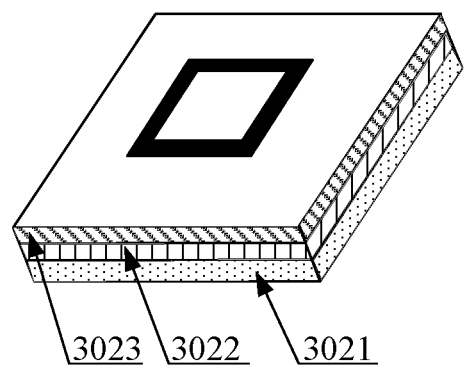
Figure 3:
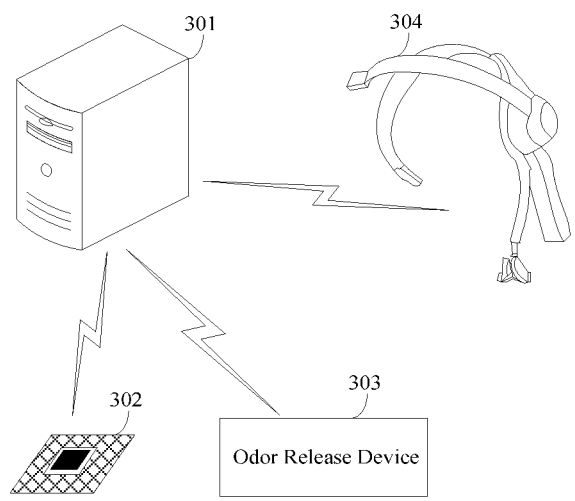
Figures 3, 4:
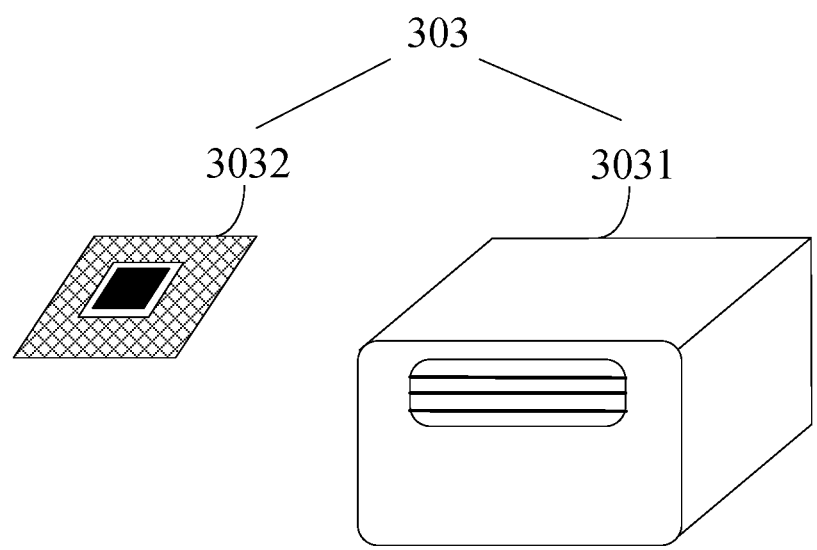

For instance, as illustrated in FIG. 3-4, the odor release device 303 may include: an odor releaser 3031 or an odor release chip 3032 disposed in the oral cavity.

The odor releaser 3031 may be provided with a plurality of containers for storing different odor molecules. When receiving the signals for indicating the target odor molecules sent by the signal processing device, the odor releaser may perform current stimulation or heating processing on the target odor molecules, so that the target odor molecules can be released into the air. The odor release device may also be provided with a fan which is configured to generate airflow at specific velocity when releasing the target odor molecules, so as to promote the release of the target odor molecules, and hence the user can feel the odor of the target food.

The odor release chip 3032 may include a plurality of functional layers, for instance, a signal receiving functional layer, an odor molecular storing functional layer and an odor molecule stimulating functional layer. Each functional layer may correspondingly achieve different functions, wherein the signal receiving functional layer is configured to receive the signals sent by the signal processing device, and the odor molecule storing functional layer is preset with a plurality of odor molecules such as ethyl acetate, hexanol and limonene. When receiving the signals, the odor release chip 3032 may stimulate the target odor molecules through the odor molecule stimulating functional layer, so that the target odor molecules can be released into the oral cavity. Moreover, the odor release chip and the airflow chip may also be integrated into a same chip. The target odor molecules released by the odor release chip may be more quickly released into the oral cavity of the human body when driven by gas released by the airflow chip, so that the user can simultaneously feel the taste and the odor of the food, and hence the effect of food simulation can be enriched.

The odor release device 303 is also configured to:

release the target odor molecules through the odor releaser 3031 or the odor release chip 3032.

For instance, the food information includes identifications of ingredients and a cooking method of food. The signal processing device 301 is also configured to:

calculate the number of the identifications of the ingredients in the food information of the target food;

determine the velocity and the consumption of the airflow for simulating the taste of the target food according to the identification of the ingredient, when the number of the identifications of the ingredients is equal to 1; and determine the velocity and the consumption of the airflow for simulating the taste of the target food by preset pattern recognition approach according to the identifications of the ingredients and the cooking method of the food, when the number of the identifications of the ingredients is greater than 1.

For instance, the food information includes identifications of ingredients, identifications of tastes, and a cooking method of food. The signal processing device 301 is also configured to:

calculate the number of the identifications of the ingredients in the food information of the target food; and determine the target odor molecules according to the identification of the taste when the number of the identifications of the ingredients is equal to 1.

For instance, when the number of the identifications of the ingredients is greater than 1, the target odor molecules are determined by preset pattern recognition approach according to the identifications of the ingredients, the identifications of the taste and the cooking method of the food.

For instance, the food signals prestored in the database are electric signals. The signal processing device 301 is also configured to: compare the waveform of the EEG signal with the waveforms of the electric signals of food prestored in the database.

For instance, the food signals prestored in the database are logical signals. The signal processing device 301 is also configured to: convert the EEG signal into a logical signal and compare the logical signal with the logical signals of food prestored in the database.

In summary, the embodiment of the present disclosure provides the food taste simulation system. The food taste simulation system may determine the food information of the target food according to the food simulation trigger signal when receiving the food simulation trigger signal, and further determine the velocity and the consumption of the airflow for simulating the taste of the target food according to the food information, and finally may release the airflow through the airflow chip disposed in the oral cavity according to the velocity and the consumption of the airflow. The food taste simulation system provided by the embodiment of the present disclosure adopts gas to simulate the taste of various foods, does not require current and temperature stimulation, improves the safety of food simulation, and enriches the effect of food simulation.

It should be clearly understood by those skilled in the art that: for convenient and simple description, the specific working processes of the system and the device described above may refer to corresponding processes in the foregoing method embodiments, so no further description will be given here.

The foregoing is only the preferred embodiments of the present disclosure and not intended to limit the present disclosure. Any change, equivalent replacement, improvement or the like made within the spirit and the principle of the present disclosure shall all fall within the scope of protection of the present disclosure.

The application claims priority to the Chinese patent application No. 201510741805.6, filed Nov. 4, 2015, the disclosure of which is incorporated herein by reference as part of the application.

The invention claimed is:

1. A food taste simulation method, applied in a food taste simulation system, comprising:
    determining food information of target food according to a food simulation trigger signal when receiving the food simulation trigger signal;
    determining airflow for simulating the taste of the target food according to the food information; and
    releasing the airflow through an airflow chip disposed in the oral cavity according to a property of the airflow.

2. The method according to claim 1, wherein the property of the airflow comprises a velocity and consumption of the airflow,
    the velocity and the consumption of the airflow for simulating the taste of the target food are determined according to the food information; and the airflow is released by the airflow chip disposed in the oral cavity according to the velocity and the consumption of the airflow.

3. The method according to claim 1, further comprising:
determining target odor molecules for simulating the odor of the target food according to the food information; and
releasing the target odor molecules.

4. The method according to claim 3, wherein the step of releasing the target odor molecules includes;
releasing the target odor molecules through an odor releaser and/or an odor release chip disposed in the oral cavity.

5. The method according to claim 3, wherein the food information includes identifications of ingredients and identifications of tastes; and the step of determining the target odor molecules for simulating the odor of the target food according to the food information includes:
calculating the number of the identifications of the ingredients in the food information of the target food; and
determining the target odor molecules according to the identification of the taste when the number of the identifications of the ingredients is equal to 1.

6. The method according to claim 5, wherein the food information also includes a cooking method of food; and the step of determining the target odor molecules for simulating the odor of the target food according to the food information includes:
determining the target odor molecules by preset pattern recognition method according to the identifications of the ingredients, the identifications of the tastes, and the cooking method of the food, when the number of the identifications of the ingredients is greater than 1.

7. The method according to claim 1, wherein the step of determining the food information of the target food according to the food simulation trigger signal when receiving the food simulation trigger signal includes:
acquiring an electroencephalogram (EEG) signal of the human body;
comparing the EEG signal with food signals prestored in a database;
determining the EEG signal as the food simulation trigger signal when the EEG signal is the same with any food signal prestored in the database; and
determining the food information of the target food corresponding to the food simulation trigger signal according to a preset corresponding relationship between the food signals and food information.

8. The method according to claim 7, wherein the food signals prestored in the database are electric signals; and the step of comparing the EEG signal with the food signals prestored in the database includes;
comparing the waveform of the EEG signal with the waveforms of the electric signals of food prestored in the database.

9. The method according to claim 7, wherein the food signals prestored in the database are logical signals; and the step of comparing the EEG signal with the food signals prestored in the database includes:
converting the EEG signal into a logical signal; and
comparing the converted logical signal with the logical signals of food prestored in the database.

10. The method according to claim 1, wherein the food information includes identifications of ingredients; and the step of determining the airflow for simulating the taste of the target food according to the food information includes:
calculating the number of the identifications of the ingredients in the food information of the target food; and
determining the airflow for simulating the taste of the target food according to the identification of the ingredient, when the number of the identifications of the ingredients is equal to 1.

11. The method according to claim 10, wherein the food information also includes a cooking method of food; and the step of determining the airflow for simulating the taste of the target food according to the food information includes:
determining the airflow for simulating the taste of the target food by preset pattern recognition method according to the identifications of the ingredients and the cooking method of the food, when the number of the identifications of the ingredients is greater than 1.

12. A food taste simulation system, comprising: a signal processing device and an airflow chip disposed in the oral cavity, wherein
the signal processing device is configured to determine food information of target food according to a food simulation trigger signal when receiving the food simulation trigger signal, determine airflow for simulating the taste of the target food according to the food information, and send signals for indicating the airflow to the airflow chip; and
the airflow chip is configured to receive the signals for indicating the airflow, and release the airflow according to the signals of the airflow.

13. The food taste simulation system according to claim 12, wherein the signal processing device is configured to determine the velocity and the consumption of the airflow for simulating the taste of the target food according to the food information, and send signals for indicating the velocity and the consumption of the airflow to the airflow chip; and
the airflow chip is configured to receive the signals for indicating the velocity and the consumption of the airflow, and release the airflow according to the velocity and the consumption of the airflow.

14. The system according to claim 12, further comprising: an odor release device, wherein
the signal processing device is also configured to determine target odor molecules for simulating the odor of the target food according to the food information, and send signals for indicating the target odor molecules to the airflow chip; and
the odor release device is configured to receive the signals for indicating the target odor molecules, and release the target odor molecules.

15. The system according to claim 14, wherein the odor release device includes: an odor releaser or an odor release chip disposed in the oral cavity; and
the odor release device is also configured to:
release the target odor molecules through the odor releaser and/or the odor release chip.

16. The system according to claim 12, further comprising:
an EEG acquisition device, wherein the EEG acquisition device is configured to acquire an EEG signal of the human body and send the EEG signal to the signal processing device; and the signal processing device is also configured to:
compare the EEG signal with food signals prestored in the database;
determine the EEG signal as the food simulation trigger signal when the EEG signal is the same with any food signal prestored in the database; and determine the food information of the target food corresponding to the food simulation trigger signal according to a preset corresponding relationship between the food signals and food information.

17. The system according to claim 12, wherein the food information includes identifications of ingredients; and the signal processing device is also configured to:
   calculate the number of the identifications of the ingredients in the food information of the target food; and
   determine the airflow for simulating the taste of the target food according to the identification of the ingredient, when the number of the identifications of the ingredients is equal to 1.

18. The system according to claim 17, wherein the food information also includes a cooking method of food; and the signal processing device is also configured to:
   determine the airflow for simulating the taste of the target food by preset pattern recognition method according to the identifications of the ingredients and the cooking method of the food, when the number of the identifications of the ingredients is greater than 1.

19. The system according to claim 12, wherein the food information includes identifications of ingredients and identifications of tastes; and the signal processing device is also configured to:
   calculate the number of the identifications of the ingredients in the food information of the target food; and
   determine target odor molecules according to the identification of the taste when the number of the identifications of the ingredients is equal to 1.

20. The system according to claim 19, wherein the food information also includes a cooking method of food; and the signal processing device is also configured to:
   determine the target odor molecules by preset pattern recognition method according to the identifications of the ingredients, the identifications of the tastes and the cooking method of the food, when the number of the identifications of the ingredients is greater than 1.

* * * * *